United States Patent
Adelberg

(10) Patent No.: US 6,422,529 B1
(45) Date of Patent: Jul. 23, 2002

(54) ROLLER CLAMPS FOR INTRAVENOUS ADMINISTRATION SETS

(76) Inventor: Kenneth N. Adelberg, 22533 Jameson Dr., Calabasas, CA (US) 91302

( * ) Notice: Subject to any disclaimer, the term of this patent is extended or adjusted under 35 U.S.C. 154(b) by 0 days.

(21) Appl. No.: 09/320,384

(22) Filed: May 26, 1999

Related U.S. Application Data

(63) Continuation-in-part of application No. 09/196,920, filed on Nov. 19, 1998, now abandoned, which is a continuation-in-part of application No. 08/646,214, filed on May 7, 1996, now abandoned.

(51) Int. Cl.$^7$ ................................................. F16K 7/06
(52) U.S. Cl. .......................................................... 251/6
(58) Field of Search ........................ 251/6, 7, 4; 604/34

(56) References Cited

U.S. PATENT DOCUMENTS

| | | | | |
|---|---|---|---|---|
| 3,802,463 A | * | 4/1974 | Dabney ...................... | 251/6 X |
| 4,047,694 A | * | 9/1977 | Adelberg ........................ | 251/6 |
| 4,340,201 A | | 7/1982 | Becker, Jr. ...................... | 251/6 |
| 4,475,708 A | * | 10/1984 | Becker, Jr. ...................... | 251/6 |
| 4,869,721 A | * | 9/1989 | Karpisek ..................... | 251/6 X |
| 4,895,340 A | * | 1/1990 | Forberg ......................... | 251/6 |
| 4,974,811 A | * | 12/1990 | Ishida ............................ | 251/6 |
| 5,190,079 A | * | 3/1993 | Nakada ...................... | 251/6 X |

FOREIGN PATENT DOCUMENTS

| | | | | |
|---|---|---|---|---|
| DE | 2855572 | * | 10/1979 | ..................... 251/6 |

OTHER PUBLICATIONS

Roller Clamp, Cutter Laboratories, Inc., 1988.

* cited by examiner

*Primary Examiner*—Lesley D. Morris
*Assistant Examiner*—Eric Keasel
(74) *Attorney, Agent, or Firm*—Sheppard, Mullin, Richter & Hampton LLP

(57) ABSTRACT

An improved injection molded plastic roller pinch clamp for IV sets includes a housing having side walls, a bottom wall, a top wall, a flow control region, a roller wheel and plastic tubing which is pinched between the roller wheel and the bottom wall. Methods for making the same and mold modifications to make the same are disclosed. A number of preferred dimensional relationships exist for achieving the easing of the effort required to adjust the wheel and consequent flow rate and obtaining a firm grip on the tube, while reducing the clamp weight. The ratio of the cross-sectional thickness of the top wall to the side wall is in the range of 1.3 to 4.0; the housing having a weight to length ratio in the range of 0.2 to 0.48 grams per centimeter (normalized range of 0.17 to 0.39), the side wall being between 1.1 and 2.3 times the thickness of the walls of the tubing. The housing is formed by a mold which may be easily modified from a prior mold to provide a wall thickness which is less than two thirds of the thickness of the upper wheel guide section. Methods for modifying molds having two cavity halves are also discussed, including processing the cavity halves to bring them closer by an amount equal to 20 percent to 70 percent of the original molded part.

38 Claims, 3 Drawing Sheets

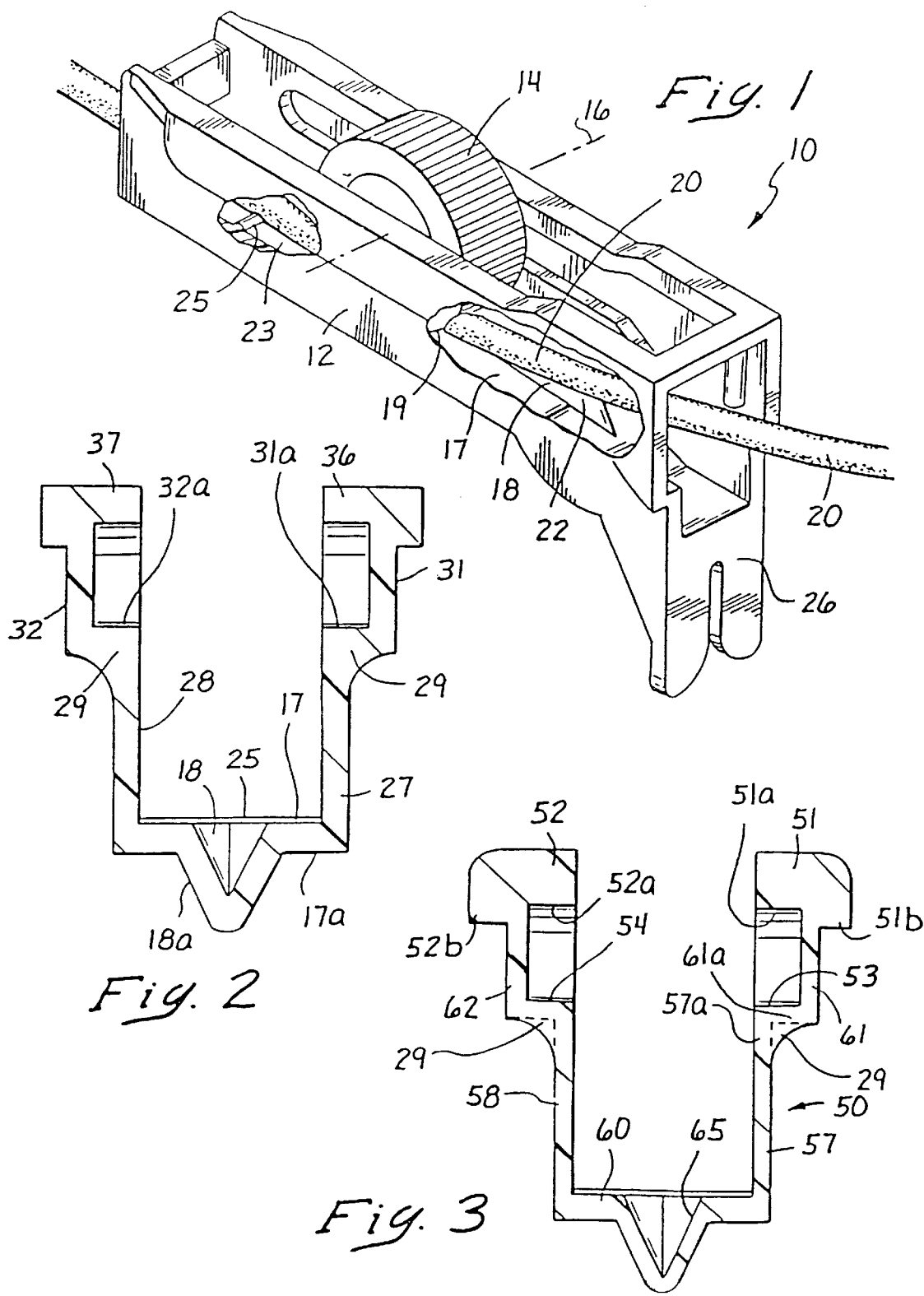

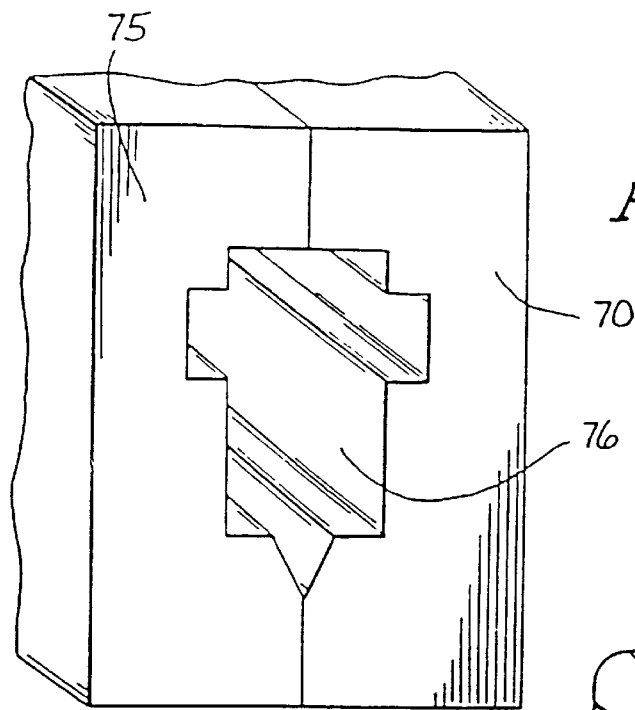
Fig. 4
Fig. 5
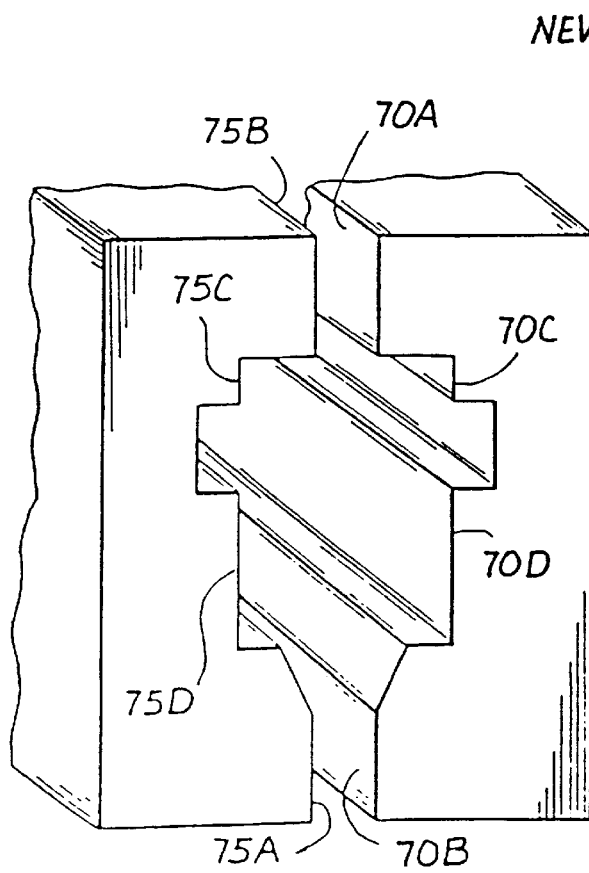
Fig. 4A

ROLLER CLAMPS FOR INTRAVENOUS ADMINISTRATION SETS

RELATED APPLICATION

This is a continuation-in-part of application Ser. No. 09/196,920, filed Nov. 19, 1998, and now abandoned, which is a continuation-in-part of application Ser. No. 08/646,214, filed May 7, 1996, and now abandoned.

FIELD OF INVENTION

The present invention relates to roller clamps for intravenous administration (I.V.) sets and more particularly to an improved roller clamp for I.V. sets having the unique combination of advantages including the benefits of diminishing the effort required to adjust the degree of pinch on the tube and improving the grip on the tube by following the preferred housing dimensional relations as hereinafter set forth as well as reduced manufacturing cost.

BACKGROUND OF THE INVENTION

Sometime during the period of approximately 1940–50, Intravenous Administration sets evolved from being reusable to being disposable. Earlier, a technique was developed to produce and store medical grade fluids for human infusion, for example, water, as well as dilute solutions of saline, dextrose, and other fluid nutrients as well as certain medicines. These fluids were stored in sealed glass containers and were administered using sterile surgical rubber tubing. The tubing and other administration components were usually re-sterilized and reused. Control of the rate of fluid administration was adjusted by varying the degree of pinch on the rubber tubing. Various pinch clamps were developed for this application.

With increasing usage, the advent of medical grade polyvinyl chloride (PVC) tubing and the need to reduce or eliminate a serious patient/hospital problem of cross-contamination, disposable administration sets were introduced. This solved the cross-contamination problem, but introduced a new one; that of time varying flow rates, i.e., variations from the initial setting of the desired flow rate over time. The pinched plastic tube exhibited the problem of creep or cold flow when pinched and this caused the flow rate to vary with time, usually this variation was large (on the order of 40 percent during the first ten minutes and increasing) and most often was a decrease in flow rate.

The first pinch clamp (which was not parallel acting) to address the time varying flow rate problem was described in about 1967, and a series of improved parallel acting clamps were introduced in the following years, as well as a number of significant refinements. The primary thrust of such newly developed clamps were, prior to 1967, ease of adjustment, and, subsequent to 1967 usually a combination of ease of use and/or adjustable flow rates which also would change little over time.

Another category of improvement was that of a clamp offering a better grip on the tube because if the clamp were accidentally released, the resultant increase in flow, or in the extreme, run away, could be life threatening or deadly.

Manufacturing cost was usually an underlying factor as is the case with most high volume usage products. Typical cost reduction factors available and employed were: (1) make parts small to conserve material, (2) use lower cost materials, and (3) make parts easy to assemble to keep labor costs-down.

Injection molded plastic is the popular approach to producing a disposable clamp. Typically, plastic materials such as Acrylonitrile Butadiene Styrene (ABS) resin or Polypropylene (PS) may be used with a rubber additive, the ABS material generally being more dense than Polypropylene or other plastics which have been used. In accordance with this invention, the preferred material is ABS or PS or PS with the possible addition of Butadiene containing polymer or other rubber like material.

The combination of economic pressures to hold down or reduce costs of health care, the enormous volume of use of infusion sets and the ever increasing cost of plastic resin combine to greatly increase interest in finding a clamp which satisfied the above mentioned need of: (1) ease of use, (2) reduce time varying flow rates and, (3) firmer grip on the tubing, as well as one which permits production at a cost still lower than that obtained by the obvious steps of making the part smaller, increasing the number of production cavities and/or using a lower cost resin.

Roller clamps for intravenous administration infusion sets, sometimes referred to as I.V. sets and typically disposed of, along with the I.V. set, after one use, are well known and are designed primarily to regulate the flow of liquid passing through a soft plastic pliable and deformable tube, usually polyvinyl chloride with a low degree of extractables. The degree of pinch of the tube is normally used to decrease and thereby regulate the flow rate to a desired value, normally measured in drops per minute when utilizing a drip chamber, the latter representing the prescribed rate at which fluid of interest is desired to be intravenously administered. These pinch clamps are also used as an on/off device, that is, either to permit flow or to stop flow. It goes without saying that the pinch clamp should, once set, accurately control the flow rate over time and also be capable of fully shutting off flow when that is desired.

Typical of the prior art clamps are those of the prior Adelberg patents, as follows: U.S. Pat. No. 4,047,694 of 1977; U.S. Pat. No. 4,013,263 of 1977; U.S. Pat. No. 3,685,787 of 1972; U.S. Pat. No. 5,014,962 of 1991; U.S. Pat. No. 4,725,037 of 1988 and U.S. Pat. No. Re 31,584 of 1984 whose disclosures are referred to and incorporated herein by reference.

In general, there have been two basic types of IV set roller pinch clamps, one being the "inclined ramp" clamp and the other being what is hereby referred to as a "parallel acting" clamp or one whose wheel travels in a generally parallel relation to what is generally referred to as a clamping surface. In each case, the clamp basically includes a housing in which is received a wheel (roller) typically supported by the housing with the plastic tube received in the housing and located between a base or clamping surface in the housing and the roller.

Regardless of the type of clamp, in one extreme position of the roller, there is "full flow", i.e., unregulated flow at the full flow capacity of the I.V. set. In another position of the roller, typically spaced from the full flow position, there is a no flow position in which there is no flow through the tubing. This typically is a shut off position. In some clamps, there is another shut off position, more properly a lock position in which movement of the roller is affirmatively prevented, as will be described, and there is no flow through the tubing. Between the full flow position and the no flow position, there typically exists a region of travel of the roller over which flow may be controlled, i.e., the region of "flow control" so called. The length of the flow control region may be less, in an axial direction, than the maximum distance over which the roller travels, especially if there is a lock position.

In the case of an inclined ramp clamp, flow control is achieved by an "inclined ramp" principle in which the roller is forced, by the operator's thumb, to climb a ramp, causing a decrease in the clearance between the roller and the opposed housing surface upon which the tubing rests, thereby creating the desired degree of pinch and thus controlling the flow rate. As the roller or wheel advances, the clearance between the roller and the surface of the housing upon which the tube rests diminishes and, in the extreme position, creates full (pinched tube) shut off. For typical flow rate settings of the clamp, the tube lumen is fully collapsed in the large center region of the tube's cross-section (where the tube radius of curvature is large), while a pair of lumens form at either side, where the radius of curvature of the pinched tube is smallest and thereby offers the greater resistance to pinch, The phenomenon of cold flow or creep in the plastic tube explains why the newly formed lumens continue to collapse and cause the flow rate to decrease, after the roller is brought to and remains in its new position.

In a parallel acting (dual action) clamp, the effects of creep or cold flow are reduced or, ideally, eliminated by having everywhere in the flow control region of the housing, a section of the housing which guides the wheel such that a tube clearance is formed which causes at any particular tube cross-section, at least one, and usually both, lumen(s) which tend(s) to form at one or both outer edges, to be fully pinched shut. Flow rate is varied by varying the cross-section of the lumen which is formed elsewhere. Fine rate control at any tube cross-section is achieved at that tube cross-section, by varying the ratio of the fully pinched shut portion of the pinched tube to that other portion which remains open, because there is a relief portion in the base or housing or wheel in which no or less, pinching is there applied. The action, or travel, of the roller need not be precisely or even nearly parallel to the opposing pinching surface of the housing. The criterion for a parallel acting clamp is to have a clearance between the roller and the housing which causes the local portion of the tube to be fully pinched shut, and to have the remaining tube portion located opposite a section of the housing surface or in some designs a portion of the outer wheel surface, which contacts or is near the tube forming a relief portion which permits and/or encourages the formation of an open lumen in the tube.

In the parallel acting type of clamp, the roller at a typical station totally pinches closed a portion of the tubing, and usually a relief in the housing is used to bring about the desired degree of pinch or partial closure of the tube. While the term "parallel" is used, it is not intended to describe a geometric parallelism or an arrangement in which the roller travel is in a precise parallel fashion over its entire range of travel; and such "parallel" action is only needed in the flow control range of roller travel. In fact, a parallel acting clamp may, and usually does, include a small relative angle between the roller travel and the opposed surface upon which the tubing rests and is clamped, for example, as a result of "draft" used in the injection mold design, as will be discussed. However, this relatively small angle is, in itself, insufficient nor is it intended to effect primary control or variation in the rate of flow since the change in clearance between the roller and the surface upon which the tube is clamped is insufficient to directly vary the tube cross-section area of flow, in contrast to an inclined ramp clamp. It is also the case that in the region of the housing before flow control and after the shut-off or no flow position, as contrasted to the lock position, the clamp action may also be non-parallel in its structure. Since these are regions other than where flow control is accomplished, the need for even approximate parallel action, as herein described, is not relevant or necessary.

Although a parallel acting roller clamp design in which only one cheek of the tube is fully pinched shut may constitute an improvement in clamps designed for good performance with respect to time varying flow rates (flow that varies over time), by fully pinching one lumen that would otherwise be formed and tend to exhibit creep or cold flow, more advanced designs fully pinch shut both cheeks of the pinched soft plastic tube.

The feature which distinguishes a parallel acting (dual action) roller clamp from an inclined ramp clamp is how flow control is achieved. Most parallel acting roller clamps achieve control of flow rate by fully pinching shut one cheek and usually both cheeks of the tube over the entire range of flow control and vary the ratio of fully pinched shut to unpinched or partially pinched, open portion of the tube according to the position of the roller in the region of flow control. It is apparent that for a given tube cross-section, fully pinching shut one or both cheeks, but not the adjacent tube section, is needed only in that range of roller travel which is effectively the flow control range. In the case of an inclined ramp clamp, flow control is achieved by varying the clearance between the roller and the opposed pinching surface. It is thus apparent that even though true parallelism may not exist in a "parallel acting" clamp, the amount of non-parallelism is insufficient to vary the clearance by any amount which substantially effects a change in tube lumen or corresponding in flow rate. This is especially true if one or both cheeks are fully pinched shut over the range of travel of the roller in the flow control region.

One typical arrangement to assure that one or both cheeks of the tube are fully pinched shut is to provide a clearance between the bottom of the roller and the opposed surface of the housing against which the tube is pinched which is generally not more than twice the wall thickness of the unpinched tubing and, in many cases, less than twice the tube wall thickness. In general, a clearance of less than twice the wall thickness operates satisfactorily to assure that one or both cheeks are fully pinched shut. Again, it is understood that this defined clearance need only exist in the flow control region. In fact, the clearance is greater at the entry end of the housing and may be somewhat less near the exit end of the housing, especially if there is a separate shut-off lock.

In the "parallel acting" clamp, the clearance between the roller and the opposed housing clamping surface may or may not vary with roller position but this variation of clearance with roller position does not substantially control the size of the formed lumen. Control, in this case, is achieved by varying the ratio of clamped shut wall portion of the soft tube to unclamped portion along the control portion of the housing.

In the inclined ramp clamp design, as the roller advances, the center section of the pinched tube may sag and be fully collapsed shut, but the clearance between the roller and the opposed housing surface: (1) is large enough to permit lumens to form, and usually, at one or both cheeks of the tube, and (2) varies to create the desired lumen size(s) and corresponding flow rate.

In a less popular version of a parallel acting clamp, the relief is in the surface of the roller. It is a general characteristic of these types of clamps that the cross sectional open area of the tubing is varied as the roller progresses along its travel, the amount of open area being related to the configuration of the relief of the clamping surface. As is known, the relief may take a wide variety of configurations and may be off to one side of the housing, or beneath the tubing or some other location usually being of varying width and or depth or both. Its function is to vary the tube open area of flow in response to movement of the roller. In effect, varying the lumen formed operates to vary the flow rate and the various parallel acting devices have this common characteristic. For purposes of this invention, "parallel acting" is intended to mean a pinch clamp having a roller and a housing and means to vary the tube lumen formed to vary the flow rate and in which there is some form of relief in the roller surface or housing or clamping surface and wherein the roller travels in a parallel relation to the clamping surface, parallel travel being as already explained.

In virtually all models and types of pinch clamps using a roller and a housing, the axle of the roller bears against a guiding surface as the wheel or roller position is altered as well as when it is in place creating the desired degree of pinch.

In the pinch clamps to which this invention relates, there are special requirements, and some of the important ones are as follows: (1) The upper surfaces of the housing should be designed to resist compression by the contacting roller axle. (2) The upper surface of the housing should be designed to resist flexure as well as outward rotation when subjected to an upward force such as that caused by the axle of a pinching wheel. (3) The side walls of the housing should be designed to withstand tension. (4) The lower surface of the housing should be designed to resist flexure as well as operate in compression, provide for a variable width relief action as well as an ideal location for tailored raised elements. The raised elements, if employed, have varying height, width and spacing. (5) The housing should be made of a plastic which can be injection molded, should have a cross-sectional area designed to facilitate flow of the injected molded plastic to fill the entire steel mold cavity and provide the rigidity needed for mold ejection, subsequent assembly, and normal use.

When parallel acting clamps were introduced to the market in commercial volumes in about 1975, the housings measured about two inches in length. The competing inclined ramp clamp housings measured about 1.4 inches in length. The parallel acting clamps captured a significant share of the market due to their better performance as compared to inclined ramp clamps and, by 1978, accounted for essentially all of the sales by one (Abbott Labs) of the two (Baxter Travenol is the other) largest firms in the United States involved with products requiring clamps for use in I.V. sets. In about 1983, Baxter started to use a patented longer clamp. Thereafter, others such as Cutter (which actually started at an earlier date), McGaw, IVAC and Borla, introduced clamps with two inch housings and a trend in clamp length was thus established.

With the more widespread use of the longer clamps, the manufacturing costs increased substantially for a large portion of the market, even though many of the longer clamps did not offer the improved performance of the patented parallel acting clamp. Some of these companies merely followed the trend to a longer housing length. In the case of the parallel acting clamps of Abbott, there was a functional reason for the length, in addition to providing non-time varying flow rate, and a firmer grip on the tubing, the longer roller travel permitted finer adjustment of the degree of pinch and thus the flow rate.

Hence, in an effort to conform to the trend to greater length, the market introduced heavier clamps, apparently showing little concern for, or giving lower priority to the consequent increase in manufacturing costs of these relatively heavier clamps. These cost increases represent a substantial sum given the number of clamps used on an annual basis.

Recently, the cost of producing a roller pinch clamp, and many other plastic items, has dramatically increased from a plastic resin cost portion being a fraction of 50 percent of the production cost to currently where the plastic resin cost constitutes a large or dominant portion of the manufacturing cost. Currently, the molding cost fraction is relatively small, and the raw material cost fraction is relatively large and growing. Thus, if the moldable, useable part can be re-designed to provide a function at least as good but utilizing significantly less plastic resin, a large savings in production costs may be realized.

Most forms of clamps have a housing whose wall thickness cross-section is fairly uniform throughout. Such a design parameter is simple to specify during the clamp's design by first focusing on the important inner surface configurations: housing pinching surface, wheel axle guide, width of wheel slot etc., and then completing the design by simply specifying a uniform wall thickness throughout.

The new form of clamp of this invention not only provides the desired type of pinch (if parallel acting, the side walls of the tube fully pinched shut etc.) but, in addition, incorporates strength (flex-modulus, etc.), and mold design (injected plastic which completely fill passages) and has a structure to achieve a substantial reduction in the material required for each clamp.

Presently, typical roller clamps have dimensions in the following ranges:

(1) Wheel major diameter width of 1.3 to 1.8 the nominal tube outside diameter, and (2) Housing wall thickness in the range of two and generally to three and greater times the undeformed soft plastic tube wall thickness, and (3) Uniform wall thickness over the entire cross-section and such cross-section being the same over the operational length of the housing where flow adjustment occurs (the region of flow control).

An obvious approach to reducing the part weight is to reduce the length of the housing. However, this is not desirable because one portion of the housing length, usually at its large end is needed to facilitate introduction of the wheel so as to make the combination operable. The remaining portion primarily serves to provide a reasonable travel range for the wheel so as to gradually pinch the tube at any position along the relief or control section of the housing.

It is not practical to decrease the overall or major width or height of the clamp housing cross-section because if done so, it will be difficult to surround and pinch a given diameter of soft plastic tube.

Present pinch clamp housings have a uniform wall thickness in the range of 0.3 to 0.5 times the O.D. of the tube for which the clamp is intended to pinch.

There is a practical minimum housing length. For popular size tubing having an outer diameter in the range of 3¼ to 4½ mm, the minimum length of the housing is in the range of 23 mm to 55 mm, or approximately 7 to 25 times the tube O.D. The wall thickness of the clamp housing is typically 1.2 mm to 1.7 mm or about 0.2 to 0.5 times the tube O.D. Most importantly, the clamp housing is usually uniform in wall cross-section thickness. This is apparently done (that of uniform housing wall thickness) because:

1. It is simple to specify.

2. It is a conventional design parameter for injection molded parts. Uniform wall thickness facilitates filling of the steel mold by the injected plastic.

3. Most clamp designs give little, consideration to variations in expected mechanical deflection of the plastic housing when subjected to the stresses associated with tube clamping.

Mechanical deflection (strain) depends upon many parameters and for a given plastic resin material, say ABS (acrylonitrile butadiene styrene), which is the preferred material in accordance with this invention, is dependent, in part, upon the level of stress and the type of stress (tension, bending, compression, torsion etc.). A good design will minimize the deflections when under load, or will, by design, allow for deflection but such deflection is to be within the elastic limit, or, if the elastic limit is exceeded, minimize the amount of deflection or degree of excess beyond the elastic limit.

When a clamp housing is put into use, i.e., assembled with a wheel and a pinched tube and the other components of an I.V. set, the expected deflections of the clamp take place, and the amount depends, in part, upon the type (tension, bending etc.) of the stress which is applied. The side walls of the clamp housing are primarily in tension while the top edge or top wall is subjected primarily to bending or flexing, with a secondary component of local compression, due to the pressure applied by the roller wheel axle where it contacts this upper surface. In the case of an injection molded pinch clamp having one or more housing wall sections in tension, according to this invention, this requires a smaller cross-section as compared with the top or bottom walls which are not primarily in tension. The distortion, or mechanical deflection of the housing, when used to pinch the tube, will be due to:

1. Primarily flexing or bending on at least two modes)of the top edge or wall of the housing.
2. Secondarily due to tension of the housing side wall.
3. To a still lesser extent, due to the local compressive force exerted directly by the wheel axle upon the upper edge of the housing where contact is made.
4. Pressure applied by the major circumference of the wheel against the lower portion of the housing surface, through the double wall thickness of the pinched soft plastic tube.

Now, if one looks to prior patents related to clamps, most patents make no written mention of side walls being thinner than the top or bottom walls of the housing and the top wall being thicker in cross-section than the bottom wall. Further the drawings of some of the patents relating to roller clamps tend to describe a variety of configurations, but offer no teaching as to why wall thickness dimensions are as illustrated. For example, U.S. Pat. Nos. 1,411,731; 1,959,074; 2,595,511; 3,135,259; 3,189,038 and 3,289,999 seem to illustrate uniform wall thickness structures. U.S. Pat. Nos. 3,099,429; 3,215,394; 3,215,395; 3,297,558 and 4,340,201 include drawings which could be interpreted as showing thin walled structure. Of these, U.S. Pat. No. 3,099,429 issued to Broman deserves special comment.

Broman illustrates a clamp with thinner top and side walls and the clamping surface or bottom wall appears to be thicker than the side walls. In Broman, the guide surface is the same thickness as the thin side wall and much thinner than the clamping surface. Broman makes no mention of weight savings, strength considerations (flexure, tension etc.). No mention is made as to why the wall thickness was as illustrated and it would appear that the cross-section thickness at the various locations was merely an arbitrary illustration.

When injection molded housings, used for roller clamps, are put to use, their side walls are generally in tension. While their top and bottom walls are exposed to a flexure or compression load because these walls in tension carry higher loads, the wall thickness needed for good design is generally thinner for the side walls. It is interesting that none of the patents cited make any mention of thinner side walls. These patents include: Dabney et al, U.S. Pat. No. 3,802,463 of 1974; Becker, U.S. Pat. No. 4,340,201 of 1982; Becker, U.S. Pat. No. 4,475,709 of 1984; Karpisek, U.S. Pat. No. 4,869, 721 of 1989; Forberg, U.S. Pat. No. 4,895,340 of 1990; Nakada, U.S. Pat. No. 5,190,079 of 1993 and German DT 28 55 572 of 1979.

A German firm named Clinico makes a roller clamp for use in Germany similar to those found on the United States market and with a weight to length ratio of 0.594 grams per cm. That clamp has a wall thickness of some 10% less than that of the U.S. clamps, yet weighs some 22% less, on the average. This weight difference in part, is due to the type of tube holder built into the clamp housing. The tube holder is at the end of the clamp at the open or input end of the clamp. In the Clinico clamp, the tube holder is much smaller than of the U.S. clamps and additionally, it is believed that the Clinico clamp is molded from a resin having a density lower than ABS.

Many commercially available clamp housings have a length in the range of 5.2 to 5.7 cm, are molded of ABS or polystyrene and have a weight to length ratio of between 0.65 to 0.72 gm/cm. By contrast, a clamp of this invention may have a length of 5.6 cm and a weight to length ratio of 0.393 gm/cm, measured in the same manner, but see the discussion below.

It is thus an object of this invention to provide a pinch clamp that is easier to adjust, provides a firm grip on the tubing, whose performance is as good as the presently available commercial clamps, one which includes a top wall which is thicker in cross section than the bottom wall and side walls are thinner than the top walls and preferably thinner than the bottom wall, as well as one which is economical to produce.

BRIEF SUMMARY OF THE INVENTION

The objects of this invention are achieved by the provision of improved roller clamps for I.V. sets and more particularly to an improved roller clamp for I.V. sets having the unique advantages of substantially reduced manufacturing cost and the benefit of good performance by diminishing the effort required to adjust the degree of pinch and improving the grip on the tube when the preferred housing dimensional relationships and the preferred relative dimensions are as hereinafter set forth.

Thus, the preferred and practical approach of this invention is to specify selectively the portions of the cross-section of the clamp housing. A refinement in accordance with this invention is to further vary the cross-section according to its location along the housing length axis. For example, the cross-section at the region of the portion of the housing designed to permit insertion of the wheel, has reduced strength requirements. In this region the wheel axle does not bear forcefully upon the opposing housing surface through a clamping action on the tubing.

Furthermore, there usually is little, or, very often, no pinch action on the tubing in this region. On the other hand in the generally longer operating section of the housing, the region of flow control so called, the structure must anticipate greater forces resulting from the interaction of the wheel, housing, and pinched tube.

Hence taking into account all of the factors discussed in connection with stresses and deflection and the like, a new and unique clamp housing design and new and improved roller clamp for use with I.V. sets, in accordance with this invention, is for the flow control portion, a housing, having:

a. thick cross-section top edge or top wall for the housing.

b. a generally thin side wall housing, as described.

c. a thick bottom wall (but not quite as thick as the top wall or the top edge) of the housing.

Important is the relationship of the ratio of the cross-sectional thickness of the top wall to the cross-sectional thickness of the side wall, which in accordance with this invention is in the range of 1.3 to 4.0.

Note that a thick cross-section top wall or edge as per (a) is used to minimize the degree of at least two types of bending or flexing as such deflection can be large and a thick cross-section will minimize this. A second justification for (a) above is to minimize the degree of local deflection or indentation of the housing surface just where the wheel axle is applying a relatively large, local force.

(b) above is used to reduce the weight of the clamp housing material and to take advantage of the fact that there is a relatively smaller deflection when under tension, and also the fact that thin plastic walls are capable of handling relatively large tensile forces.

(c) above is used to stiffen (but no more than is necessary) the bottom wall to accommodate bending and flexing. Parameter (a) above is designed for the housing to be subjected to a relatively large force causing bending and flexing, which force is applied by the wheel axle. Parameter (c) is designed to respond to a similar opposing force, also causing bending and flexing, but this force is more distributed because it is transmitted and applied by the pinched section of the soft plastic tube, and also because this surface is wider.

The greatest degree of flexing will take place when the wheel is centrally located between, and thereby approximately equally distant from, the end supports of the housing. Thus, the axially centered portion of the upper wall portion should be correspondingly thicker than at either end. However, this is not practical for injection molded parts as a "draft angle" of the part will not be present to permit removal of the just molded part which when conventionally injection molded, will shrink to firmly grasp the mold core. A practical compromise, however, is a design where the wall thickness of the housing is diminished near the small end of the housing, but not diminished as much at the open end of the housing.

Creep or cold flow may take place in the wheel and housing of the pinch clamp (it usually takes place to a greater extent in the pinched soft plastic tubing). To An:exist, the load applied must cause the part to exceed its elastic limit. If creep or cold flow exists, the part dimension may change with time, with no external changes in the load and this will contribute to a time varying flow rate of the fluid through the pinched tube. To avoid this undesirable phenomenon, the load should be limited, or the wall cross-sections sufficiently large (and correspondingly strong) so as to prevent exceeding the elastic limit or minimize the stress. On the other hand, deflections must be anticipated because strain usually accompanies stress. It is usually best to attempt to operate within the elastic limit.

Since the part described in this invention is made of plastic and preferably molded, for proper injection molding, a "fill" cross-section or tunnel is needed in the part to assure that the molten plastic resin, usually at a temperature in the range of 350° F. to 500° F., will readily flow so as to rapidly and entirely fill the cavity. If the tunnel or fill cross-section is too small, the molten plastic will cool too rapidly and freeze prior to there being a complete fill. At lower temperatures, the injected plastic resin's viscosity, which is very temperature dependent, will be so high that a partial fill may result. Too large a tunnel or fill cross-section will eliminate the partial fill problem but will result in a part using excessive (and costly) plastic resin and also will unnecessarily increase the time (and thereby the production cost) required to cool the injected plastic to a temperature permitting ejection of the formed part from the mold cavity and still be able to retain its newly formed shape (no warping etc.). A long residence time in the mold increases the molding cost, usually in a linear manner. That is, if the cycle time to produce the molded part by the molding machine is doubled, the molding cost is approximately doubled.

Insofar as the molding operation and mold design are concerned, it is important to the present invention to properly select and combine the size and location of the fill cross-section or fill tunnel having the properly designed cross-section as to provide both the needed strength when the part is later called upon to perform by being sufficiently rigid or strong in the bending, flexure or tensile mode as well as to provide a fully formed part. Thus, the preferred form of the mold for proper molding has internal cavity and external core surfaces sized and located and serving the independent requirements of having:

(1) A properly sized and located fill tunnel or fill cross-section adequate but not so large as to unnecessarily increase the part weight and/or slow the production cycle.

(2) A properly sized and located flexure or tensile cross-section to provide the desired strength, rigidity or flexure, just adequate but not too large.

(3) Walls having suitably thin cross-section satisfying other demands of tensile strength and part integrity, yet utilizing the minimum plastic so as to keep the total weight low and also to facilitate a short cooling time for a faster production time. Faster production time makes possible larger production volumes for a given mold time interval and machine, typically a doubling of cross-section increases the molded part cooling time and corresponding cost of molding approximately fourfold.

As explained above, the housing top wall is made thicker so as to have the strength necessary to have the needed flexural rigidity and to prevent excessive penetration (indentation) due to the local force of the wheel axle.

By way of explanation, should the top wall or top rail have a thickness less than a minimum value, the penetration of the wheel axle may be so large as to cause a permanent deformation resulting in time varying flow rates through the pinched tube, due to creep or cold flow of the plastic forming the top rail/wall of the housing. This creep and cold flow results when the plastic used to mold the housing exceeds its elastic limit. Excessive penetration will also make it difficult for the operator to adjust the wheel position. This is because a deeply penetrating axle will require a relatively large force to advance the wheel to a new location. A plastic material with a high value for Rockwell hardness will offer the best resistance to local penetration by the wheel axle, but plastic material cost and moldability may detract from the contribution of a large value of hardness.

In accordance with this invention, the top wall or rail of the housing, when used under load or in use, must withstand three types of deformations. The primary task is to resist flex over the entire length of the housing while applying the desired clamping force upon the roller axle. In addition, as mentioned, the top wall must resist excessive wheel indentation of the wheel axle into the local surface of the top wall, i.e., the top of the trunnion groove. A third consideration is resistance to outward rotation of the top wall leading to "pop out" of the wheel, as will be discussed. In each of these cases, it is important that for the top wall not to exceed the appropriate elastic limit.

However, a thick wall section generally requires a longer time to cool, a necessary step in injection molding. This longer cooling time makes for higher manufacturing cost because of longer mold cycling time. All of the above is correct and true where the cooling is one dimensional, such as is the case for a part having a thickness small compared to its other two dimensions.

However, where one other dimension, perpendicular to the thickness dimension, compares with the thickness, the cooling, effectively, is two dimensional and correspondingly requires much less time. Thus, to avoid excessive cooling times, the thick wall top portion should have a thickness comparable to its width. This serves a double function of providing for the more rapid two dimensional cooling as well as providing a generous flow passage for the injected molten plastic facilitating a complete fill of the adjacent thin side wall portion of the housing.

Another aspect of this invention is the relative ease by which currently existing molds may be modified to obtain the benefits of this invention. One feature includes a relatively simple change to the injection molding cavity by bringing the two cavity halves closer together to produce thinner side walls (which must withstand tensile forces in use).

Another feature includes (1) shifting the mold core with respect to the cavity to (a) increase the wheel axle guide portion thickness of the housing (to provide needed flexural strength as well as resistance to penetration by the wheel axle), (b) locate the injection molding gate so as to assure good distribution of molten plastic, (c) significantly reduce the housing clamping surface wall thickness (because of its inherently larger wall cross-sectional area), (d) introduce or retain two dimensional heat transfer (cooling) where the wheel axle guide in the housing has its thicker wall cross-section (so as to keep down production molding cycling time).

In the case of the housing, over the range of flow control, the cross-section of the housing in accordance with this invention is such that:

1. Side wall thickness is in the range of 1.2 to 2.2 times the undeformed (nominal) soft plastic tube wall thickness (and not 2.2 to three times).
2. Top wall thickness (wheel axle guide) is 2 to 3.3 times the undeformed soft plastic tube wall (this is in the typical range or thicker).
3. Bottom wall thickness is preferably less than that of the top wall (as opposed to being generally equal).
4. Side wall thickness of approximately 0.3 to 0.6 that of the top wall thickness (as opposed to being generally equal). As noted earlier, the ratio of the cross-sectional thickness of the top wall to the cross-sectional thickness of the side wall is in the range of 1.3 to 4.0.

Further details are hereinafter set forth. In this way, the objectives noted above are achieved.

This invention has many other advantages, and other objectives, which may be more clearly apparent from consideration of the various forms in which it may be embodied. Certain versions of such forms are shown in the drawings accompanying and forming a part of the present specification. These forms will now be described in detail for the purpose of illustrating the general principles of the invention; but it is understood that such detailed description is not to be taken in a limiting sense.

BRIEF DESCRIPTION OF THE DRAWINGS

FIG. 1 is a view in perspective of a typical prior art clamp;

FIG. 2 is a sectional view of the current form of pinch clamps as used in the prior art;

FIG. 3 is a sectional view of a clamp housing in accordance with this invention;

FIG. 4 is a diagrammatic view of the mold of the prior art;

FIG. 4A is a view similar to that of FIG. 4 illustrating a mold in accordance with this invention; and FIG. 5 is a diagrammatic view comparing one form of modification (left side) of the new part to illustrate the effect thereof (the right side illustrates a conventional cross-section for comparison);

DETAILED DESCRIPTION OF THE INVENTION

Figure 6:
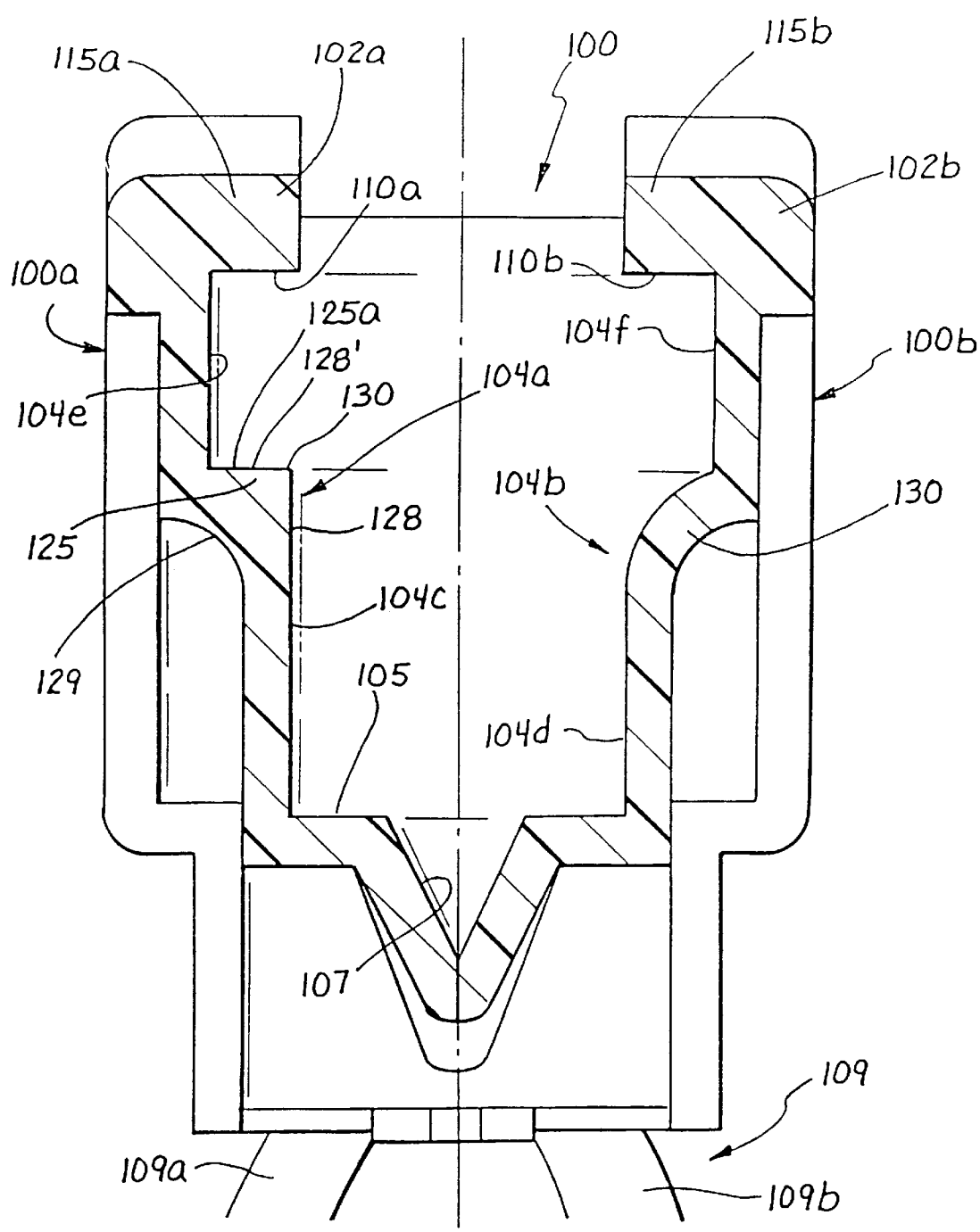
FIG. 6 is an enlarged diagrammatic view of a preferred form of the transition zone in accordance with this invention (right side) as compared to another form of transition zone (left side) in accordance with this invention.

Referring to FIGS. 1 and 2, a prior art parallel acting clamp 10 is illustrated for the purposes of explanation, although it is understood that the present invention may also be applied to an inclined ramp clamp. The clamp 10 includes a housing 12, a wheel in the form of a roller 14 having a wheel axle 16 received in grooves formed in the upper portion of the housing. In this explanatory form, the housing includes a lower surface or bottom wall 17, the latter provided with a groove 18, a V-groove being shown for purposes of illustration, the space between the bottom of the roller and the surface 17 receiving a tube 20 through which fluid flows in a controlled manner based on the position of the roller.

The majority of roller clamps have a simple wheel whose width of its major diameter compares with one-half of the circumference of the tube to be pinched, and axles which protrude out from each side of the wheel. The housing channel usually has a bottom surface (the upper surface of the bottom wall) having a width wide enough to accommodate both the pinched tube and the width of the pinching wheel. Side walls of the housing are usually adjacent the bottom channel or wall and form the lower side walls which act to guide the tube to be pinched so as to be located between the wheel and the housing pinching surfaces. Away from the housing channel or bottom wall of the housing and opposite the wheel axles, the housing side walls include a trunnion section to receive and guide the axles.

The upper surface of the inner trunnion wall usually runs more or less parallel (more so for a parallel acting clamp, less so for an inclined ramp clamp) to the lower housing pinching wall (bottom channel or wall), and is interrupted to form a slot through which the upper portion of the wheel protrudes. The result is that there is usually found two generally distinct portions of the housing side walls; the major lower portion, as well as a smaller upper portion containing the trunnions and the side end walls of the trunnion. The trunnions have a trunnion side end wall opposite the outward end of the wheel axle and a spacing (height) to just accommodate the wheel axle diameter. An upper and lower portion of the trunnion portion each usually have a span (width) compared to the projection length of the wheel axle.

The inner upper surface of the trunnion often runs more or less axially of the housing clamping surface or bottom wall and, when the tube is being clamped, bears the local compressive load applied by the protruding wheel axle. To spread this localized axle load, the wheel axle is shaped like a cylinder, having a uniform diameter throughout its protrusion length. This concentrated bearing load would tend to be even more concentrated if the protruding axle were not of uniform diameter.

Accordingly, the upper surface of the inner trunnion side is required to have a generally sharp 90° corner where it joins the inside face of the vertical trunnion side end wall, which right angle generates a stress concentration during tube pinching. Another region of stress concentration is located where the lower portion of the trunnion inside side end wall joins the inside of the lower end wall. Due to the need to maintain a uniform diameter of the protruding wheel axle, a radius or curve or fillet cannot be placed where the inside upper surface of the trunnion meets the vertical portion of the trunnion side end wall.

The material of the tube is usually plasticized polyvinyl chloride of the type heretofore used in I.V. sets, although other medical grade plastic tubes may also be used. Typically such tubes have an I.D. of about 2.3 mm to 3.0 mm, an O.D. of from 3.5 mm to 4.5 mm and a Shore D hardness exceeding about 68 and usually under 80. A tube of the type described may also be used with the clamp of this invention. The groove 18 is one of varying cross-section along its length to vary the cross-sectional tube area through which fluid may flow.

For this parallel acting clamp illustration, the wheel functions to fully pinch shut the side walls of the tube for the reasons discussed and the variable cross-section groove serves to vary the open portion of the tubing to adjust fluid flow rate. In the form illustrated, the region of flow control extends from about region 22 to region 23, the lower surface including a raised perpendicular element 25 at the far end of the clamp which operates as a lock to assure complete shut off, even though the shut-off zone is immediately upstream of the element 25. In effect, there is also no flow with the roller positioned in the region at the end of the groove and prior to the bump. In this form, the travel of the wheel along its path is generally close to, but not necessarily precisely, a parallel relation over the region of flow control by the provision of axle grooves on the outer periphery, as shown, which are basically in nearly, or exactly, parallel relation to the surface 17 in the region of flow control. The travel of the wheel over the element 25 is non-parallel, but there is no flow control in this region, as discussed. Typically, the clearance between the bottom of the wheel and the surface 17 is generally less than and not greater than twice the nominal wall thickness of the tubing 20 used with the clamp. Since tubing of a variety of sizes may be used, the clearance between the surface 17 and the bottom of the wheel in the flow control region may vary from one type of clamp using one size tubing to another to maintain the full pinch on each side of the tubing. There are also clamp structures, not illustrated, in which only one side of the tubing is fully pinched shut since, in such a design, the flow lumen is off to one side. Also shown, at the large end of the housing, away from the perpendicular element 25, is the tube holder structure 26.

Referring to FIG. 2, it can be seen that the housing is of a substantially uniform cross-section of about 0.3 to 0.6 times the tubing O.D., typically between 1.2 mm and 1.7 mm, the length of the housing being between 20 mm and about 55 mm. The uniform cross-section can be seen from the cross-section of the bottom wall 17a which forms surface 17 and the wall 18a in the portion of the bottom groove 18. The lower side walls 27 and 28 of the housing are essentially of the same cross-sectional thickness as the bottom wall 17a and the groove wall 18a. There is a transition zone 29 between the lower walls 27 and 28 which includes a portion having the cross-section of walls 27 and 28 and trunnion wall portions 31 and 32 which form the side end walls of the trunnion grooves in which the wheel axle 16 travels. The transition zone 29 operates to distribute better the stress between the trunnion wall and the walls 27 and 28 below the trunnion walls. This transition zone includes and forms the lower shoulders 31a and 32a of the grooves on which the wheel axle 16 travels. Above the shoulders 31a and 32a are the top edges or top walls 31 and 37 of the housing, the latter forming the upper portion of the trunnion groove. As seen in prior clamps, these top edges or walls have a cross-sectional thickness basically equal to that of the sidewalls 27 and 28. Thus, the top wall 36 and 37, lower side walls 27 and 28, the trunnion walls 31 and 32 and the bottom wall 17a, as well as the groove 18a all basically have the same cross sectional dimension.

As seen in FIG. 2, the trunnion end side walls 31 and 32, which are actually part of the side walls, but smaller in vertical length than the overall side wall, are basically parallel to the lower side walls 27 and 28. Note, however, that trunnion side end walls are generally parallel to and spaced outwardly from the lower side walls 27 and 29 in order to accommodate the axle of the wheel, the axle being on the inside of end side walls 31 and 32.

It will also be seen that the junction between the side end walls 31 and 32 and the underside of the top walls 36 and 37 which form the upper trunnion wall are basically at a sharp angle, e.g., a right angle, as is the case with the junction between the side end walls 31 and 32 and the lower trunnion walls 31a and 32a, respectively. These sharp angles, illustrated as right angles on the inside of the side end walls and the top and bottom of the trunnion grooves form stress concentration regions and generally cannot be curved or arcuate to reduce stresses which tend to exist at these junctions since the wheel axle has a cylindrical shape and should travel in a true linear manner axially along the clamp body. The use of a tapered or varied cross-section wheel axle is not practical because of the need for maximum contact which cannot readily be achieved with a tapered wheel axle which generally follows the contour of any fillets or radii at the inside corners between the top trunnion guide, the trunnion end side walls and the lower trunnion guide and the trunnion side end walls immediately above the lower trunnion guide. However, in the case of transition zones 29, located on the outside of the side end walls and the lower end walls, a transition zone may be provided, as shown, to reduce stress concentration since it does not interfere with clamp operation and tends to relieve stresses in what normally would be a region of relatively high stress concentration.

A wall subjected to tension or flexure and having a corner or abrupt change in direction will have a region of stress concentration at the corner making that portion exposed to stress greater than the adjacent portion and so, closer to structural failure. Where it is not practical to use a radius, curve or fillet, use has been made of thicker walls at the joints or junctions of the walls to provide a higher strength region. This, however, is to be minimized since it also tends to increase the weight of the clamp body.

Referring to FIG. 3, a preferred form of the roller clamp of this invention is illustrated, again in the form of a parallel acting clamp having the parts, housing, V-groove, wheel tubing etc., already described. For purposes of description, however, only the housing 50 will be discussed. The clamp housing cross-section may be divided into three zones, each to satisfy individual and special requirements in accordance with this invention in order to reduce weight while maintaining performance, especially in terms of ease of adjustment and better gripping of the tubing, due in large part to utilizing the dimensional ratios as set forth and the ranges and the various relationships described.

The top zone which includes the region including the top edges or walls 51 and 52, the portion above the trunnion shoulders 53 and 54 and above the underside of the upper trunnion walls 51*a* and 52*a* and above walls 61 and 62. The top walls 51 and 52 include side portions 51*b* and 52*b* which extend slightly below the underside of the upper trunnion walls 51*a* and 52*a* and which also form part of the top wall and the top zone. The top zone should be capable of withstanding a local indentation, a flexure load (arching) as well as resisting an outward rotational moment due to tube clamping and imposed by a wheel axle whose position varies over the length of the housing. Thus, the top wall has a cross-section which is at least 20 percent thicker than the side walls. The trunnion of the wheel bears against the underside 51*a* and 52*a* of the top edges or walls during a clamping operation. The undersides should be capable of withstanding penetration of the wheel axle or trunnion as a consequence of the clamping action and imposed by the wheel axle which has a relatively small radius of curvature. This localized penetration typically is in the form of local indentation by the wheel axle. A less obvious requirement is that during molding a flow passage be provided for injection of molten plastic to flow through a large part of, or, ideally, the full axial length of the part without being exposed to a large contact area which contact area causes cooling and if too large, consequent premature solidification. There is also required a lateral flow to form the side walls 57 and 58. Additionally, to facilitate flow, the cross-section of the top edges 51 and 52 approach being circular in cross-section, as illustrated.

The second zone is the side zone which includes basically the lower side walls 57 and 58 and the wall portion including the shoulders 53 and 54 forming the horizontally disposed bottom walls of the trunnion grooves and groove walls or upper wheel axle guide wall sections 61 and 62 which extend below the lower side portions 51*b* and 52*b* of the top wall 51 and 52. The transition zone is that portion of the side zone between bottom side walls 57 and 58 and the trunnion side end walls 61 and 62, and correspond to curved transition zones 29, as previously described and explained. The transition zone in accordance with this invention is located on the outer portion of the housing, as shown, becomes progressively thicker from just inside the outside face of the side end walls 61, 62, reaches a maximum at the intersection of the side end walls and the adjacent lower side walls 57, 58, and progressively diminishes to the cross-section of the lower side walls 57, 58.

As seen in the dotted lines in the right hand portion of FIG. 3, for purposes of illustration, it being understood that the same applies to the left hand portion, the section 61*a* of the side wall 61 below the lower trunnion 53 is substantially of the same cross-sectional thickness as that of the side wall 61. The section 57*a* of the lower side wall 57 joins to the section 61*a* and is integral therewith, section 57*a* being substantially of the same cross-sectional thickness as side wall 57. In accordance with this invention, the external fillet or radius 29 extends the length of the trunnion groove and represents only a relatively small amount of weight since the exterior radius of the fillet preferably does not exceed twice the thickness of the lower wall 57. This is in contrast to some prior art roller clamps in which there is no radius, but the transition zone is square.

This side zone must possess sufficient strength to properly withstand the tensile forces to which it is exposed during use resulting from the clamping action generated within the clamp housing. The side zone must possess a lesser, but nonetheless, sufficient flow cross-section for the injected molded plastic to flow the vertical distance to properly fill the side zone portion of the housing without premature cooling and thereby solidifying prior to filling this region. Depending upon the location of "gates" which first admit the molten plastic into the cavity, the side may also be required to have a flow cross-section to fill an adjacent zone, not served by its own gate.

It is to be noted that the surface area of the trunnion side end walls 61 and 62 is less than the surface area of the bottom lower side walls 57 and 58. One could make the cross-sectional thickness of the trunnion side end walls less than the cross-section of the lower side walls and thereby reduce the overall weight of the clamp. Conversely, the lower side walls could be thinner in cross-section than the cross-section of the trunnion side end walls.

In accordance with this invention, the cross-sectional thickness of the trunnion side end walls is approximately equal to the lower side walls and is preferably between 0.8 to 1.2 times the cross-sectional thickness of the lower side walls, provided the other dimensional relations discussed herein are also used. In one preferred form of this invention, the cross-section of the trunnion side end walls 61 and 62 is essentially that of the lower side walls 57 and 58, again provided the other dimensional relationships discussed herein are also used. Except for the two stress reducing material additions (transition 29), the wall thickness of the trunnion vertical side end walls (61, 62) and that of the lower walls (57, 58), should have, for minimal weight, equal thickness because they each carry the same tensile load. The cross-sectional thickness of the top wall is preferably between 1.3 and 4.0 times the cross-sectional thickness of the side walls.

The bottom zone which basically includes the bottom wall 60 and the wall portion formed by the relief groove 65 should be capable of withstanding flexure loads similar to the top zone. The bottom wall has a cross-sectional thickness which is greater than the side walls. It is also the case that the end of the bottom wall beyond the shut off position and the lock position is slightly tapered. This taper is well beyond the region of flow control and is basically between the limit of roller travel and the far end of the clamp body.

The flexure load of the bottom zone is similar to that of the top zone, however, because the flexure load applied to the bottom zone is applied through the major diameter of the wheel which, in turn presses through a double layer of soft plastic tubing, the need to resist a penetration load is greatly reduced.

Furthermore, since the cross-sectional area of the bottom zone has a greater transverse width (left to right) than the combined transverse widths of the left and right top zones, the cross-sectional thickness of the bottom zone may be smaller to achieve the cross-sectional area required to withstand the flexure load.

Thus, in an ideal form, the top wall is thicker than the side walls by at least 30 percent, the trunnion end side walls and the lower end walls are of substantially the same cross-sectional thickness and the bottom wall is thicker in cross-section than the lower side walls and the upper side end walls, but thinner in cross-section than the cross-section of the top wall.

Still other loads and requirements ought to be met. However, these are usually accommodated (with a reasonable safety margin) if the above mentioned requirements are properly satisfied.

As already noted, the housing regions of the top zone, in accordance with this invention, are greater in cross-sectional dimension than the regions of both the side zone and the regions of the bottom zone. The regions of the side zone are thinner in cross-sectional dimension than the regions of the top zone and the regions of the bottom zone. The regions of the bottom zone are thicker in cross-section than the regions of the side zone but of less cross-sectional thickness than the regions of the top zone. In a preferred form, the end walls 61 and 62 of the trunnion grooves, which form part of the side zone, are of a cross-section of about the same as that of the side walls 57 and 58, it being understood that walls 57 and 58 need not be of the same cross-section but should be less than the cross-section of the bottom wall 60.

These requirements may be met with dimensions for the housing expressed in various relations in the approximate ranges as set forth:

(1) Side wall thickness of 1.1 to 2.3 times the undeformed (nominal) soft plastic tube wall thickness;

(2) Top wall thickness of 2.5 to 4.5 times the undeformed soft plastic tube wall thickness;

(3) Bottom wall thickness of 0.4 to 1.0 times the top wall thickness;

(4) Side wall thickness 0.3 to 0.8 that of the top wall thickness;

(5) A clamp housing weight to length ratio of equal to or less than 0.48 grams per centimeter, preferably in the range of 0.48 to 0.2 and optimally in the range of 0.3 to 0.4 clamp housing weight (grams) to length (centimeters) ratio, and a strength capable of pinching fully shut a PVC tube with an I.D. of 2.28 to 3.18 mm and an O.D. of 3.0 to 6 mm having a Shore D hardness in the range of 65 to 90 and an uncompressed wall thickness in the range of 0.5 to 1.0 mm;

In terms of the normalized parameters, wherein the weight to length ratio is also divided by the specific gravity of the plastic, the above values for ABS are modified as indicated below:

Weight to Length ratio for ABS;
General range: 0.48 to 0.2 gm/cm
Preferred range: 0.3 to 0.4 gm/cm.

Weight to length ratio for all plastics:
General range: 0.39 to 0.17 gm/cm
Preferred range: 0.25 to 0.33 gm/cm.

(6) An upper and lower side wall thickness of less than two thirds the thickness of the wall in the upper wheel guide section in that region of the housing forming the flow control region, as previously described;

(7) An upper and lower side wall thickness of less than the thickness of the bottom wall thickness;

(8) An upper and lower side wall thickness of less than ¼ of the width of the major diameter of the wheel;

(9) An upper and lower side wall thickness of less than 2 ½ times the wall thickness of the (pinched) tube when the tube is in an undeformed state;

(10) An upper and lower side wall thickness to top wall thickness ratio of less than 0.7 over the length of the clamp housing where flow through the tube is controlled;

(11) A top wall so dimensioned that its thickness to width dimension, in cross-section is in the range of 0.5 to 1.0;

(12) A bottom wall of 1.2 to 2.5 times the uncompressed tube wall thickness, and

(13) A wheel width of from 0.175 to 0.270 inches.

The clamp housing may also have a top wall wheel guide section whose cross-section has a width to height ratio of less than 2.0.

From the above, it is apparent that this invention encompasses a clamp housing whose top, side and/or bottom wall thickness is reduced in the region of no control (entrance section and past the full shut off) when such wall thickness(es) are compared to the thickness of a corresponding part in the region were the tube may be pinched to achieve flow control or shut off.

From the above description, it is apparent that the regions of the side zone represent a substantial portion of the clamp structure and thus reduction in the cross-sectional dimension of the regions of side walls, e.g., walls 57 and 58 and the trunnion walls 61 and 62, operates to reduce the weight of the clamp. The cross-sectional dimension of each of 57, 58 and 61 and 62 need not be the same, but each should be less than the cross-sectional dimension of the bottom wall 60. In a preferred form each of 57, 58 and 61 and 62 are of the same cross-sectional dimension, as described. In accordance with this invention, the walls of the V-groove 65 may be of a lesser cross-sectional dimension than that of the bottom wall 60 and less than the regions of the top zone, and in a preferred form are less than the cross-section of the bottom wall and of about the same cross-sectional dimension of the walls 57 and 58.

Another aspect of the present invention is the ability to up-grade an existing mold and implement the present invention for a mold which produces housings for a roller type pinch clamp which now can be modified to include many of the desirable features of the present invention. The approach described is applicable to either an inclined roller clamp or a parallel acting clamp.

Typical prior art clamp housing cross-sections are illustrated in FIG. 2. FIG. 3 illustrates a preferred embodiment in ranges described for this invention. Note that in comparing the structure of FIG. 2 with that of FIG. 3, in the structure of the present invention, the upper wheel guide surface (51, 52) is enlarged in cross-section, the lower clamping surface 60 is essentially unchanged or slightly thinner, and the lower side walls (57, 58) thickness and the upper portion of the upper side end walls (61, 62) is greatly diminished and the top wall has the greatest cross-section, as already described. FIG. 5 is an illustration that facilitates the comparison.

The lower clamping surface (walls adjacent to the V-groove relief groove) can and should be made thinner than the upper (top wall). This is because its width is greater than that of the upper wheel axle guide surface. Both the upper and lower surfaces are subjected to approximately equal flexural forces. Resistance to flexure is, with other dimensions being similar, nominally proportional to the cross-sectional area. Hence, a thinner section is preferred for the bottom clamping surface for a balanced structural design.

The upper wheel guide surface has, because of the opening to permit wheel travel, a width smaller than the lower surface and, to assure proper resistance to flexure resistance to outward rotation and also resistance to indentation by the wheel axle, this upper wheel guide thickness and cross-section should be increased.

The side wall cross-sectional thickness is greatly diminished by utilizing a thin wall. This is because the primary load of the side wall, when the clamp is in use, is tensile. For ABS, polystyrene, and other thermoplastics in popular use such as SAN, rigid acetals and nylons, the tensile strength is relatively great and their modulus of elongation is relatively small. Hence by properly designing for the application, a substantial weight saving is enjoyed.

In manufacture, nearly all infusion set roller clamp designs are intended for injection molding. Their interior and exterior surfaces are tapered (have a draft) to facilitate easy ejection from the mold, can usually be made with simple two plate molds, etc. In the case of a parallel acting clamp, this draft provides a small angle on what is sometimes called the clamping surface; however, this small angle (for example, in the range of ½ degree) plays no part in flow control as already discussed. The intended function; ease of use, ease of adjustment, tight tube gripping etc., is all determined by the design of the mold core. It is the core which forms the interior configuration and dimensions of the housing. The core dimensions, shape, dimensional tolerances, etc., determine the clamping performance of the molded part. It thus appears likely that, for nearly all roller clamps, the function of the designed part focuses on the core; and the cavity shape, dimensions, etc., are usually derived by simply specifying a uniform wall thickness for the part which typically is in the range of 0.045 to 0.060 inches.

By contrast, in accordance with the present invention, the key elements constituting the improvement have nearly everything to do with the cavity design and little, if anything to do with core design. To convert an existing mold, the cavity halves mating surfaces are slightly shaved, as has been and will be further discussed, and then rejoined. The cavity is also slightly shifted with respect to the core. The core is left essentially unchanged, but the gate(s) is/are relocated to permit feeding of injected plastic to the, now thickened, wheel guide surface.

A typical housing cavity in a mold is constructed in a clam shell fashion and often the two halves 70 and 75 are nearly or exactly symmetrical, see FIG. 4. As is known, a mold core is also used which is located in the cavity 76 in a molding operation. To modify a design of a prior art mold used to produce one of the prior art clamps, two relatively simple steps are required to produce a modified mold for production of improved clamps in accordance with this invention.

1. The mating halves of the cavity need to be shaved by a relatively small amount, so as to produce a new housing wall thickness, on the order of 40 percent to 80 percent of the original wall thickness. In FIG. 4A this is shown by shaving off the surfaces 70A and 70B and 75A and 75B. Should the part wall thickness already have a typically modest taper (slightly thinner at the small end of the housing and typically slightly larger at the larger end of the housing then such taper should remain; a typical draft would have the wall thickness vary by a few thousandths of an inch for each inch of length. A draft is used to facilitate removal of the part from the mold.) This slight taper usually can be preserved by taking (shaving) off an equal depth of material all along the contact surface of the cavity half.

2. With the cavity halves apart, as seen in FIG. 4A, a small amount of material can be removed from that portion of the mold surface which forms the external portion of the wheel guide on the molded housing. In FIG. 4A, these surfaces are identified as 70C and 75C. Since this is done on only this special area, certain important dimensions of the molded part such as the critical shape formed by the mold core, are not altered.

The effect of the above is to move each half of the cavity halves closer together by an amount equal to 25 percent to sixty percent of the original molded part side wall thickness. The vertical shifting of the core is typically in the range of 20 percent to 70 percent of the original top wall thickness.

These two steps are relatively simple to perform and can be done rapidly and at low cost. Following this approach, there is little need to modify the usually more expensive core portion of the mold. The already less costly cavity portion of the mold need only undergo a relatively minor procedure. All this may be contrasted with the much higher cost of construction of a new multi-cavity mold.

As mentioned previously, one of the potential problems of prior art roller clamps is "pop out". Referring to FIG. 6, a partial view of a clamp housing 100 for a parallel acting clamp is shown which includes a left hand section 100a and a right hand section 100b for comparison purposes. As described, the housing includes top walls or rails 102a and 102b, side walls 104a and 104b, the latter including lower wall sections 104c and 104d located below the side wall portions 104e and 104f, the latter forming the trunnions which receive the axle of the wheel, not shown. Located between the side walls 104a and 104b and below the top walls 102a and 102b is the bottom wall 105, with a V-groove 107 therein, as previously described. Also shown partially is a form of tube holder 109, similar in function and location as 26, but basically composed of curved fingers 109a and 109b, open at their ends for passage of the tube.

With a tube assembled in the housing, it rests on the bottom wall while the axle of the roller is received in the trunnions 104e and 104f. The roller is urged downwardly by the axle which bears against the upper trunnion walls 110a and 110b. It can thus be seen that the force acting on the bottom wall 105 is not aligned with the upper force on the upper trunnion walls 110a and 100b with the result that a rotational moment indicated by arrows 115a and 115b is created. This rotational moment tends to pop the axle out of the trunnion if the top wall or rail is incapable of resisting this force. A stiff top rail will resist pop out, but such resistance depends upon the cross-sectional thickness of the top rail and the modulus of the material used for the housing. The use of side walls that are thinner than the top walls also tends to promote ease of wheel adjustment while the wheel firmly grips the tube due to the relative stiffness of the top wall.

It can be shown by a simplified model that the rotational deflection is proportional to the third power of the top wall thickness. Accordingly, large benefits may be expected by modestly increasing the thickness of the top wall or rail. Moreover, since the flow rate through the orifice of the pinched tube is proportional to the second or third power of the hydraulic radius, a change in pinching clearance as a result of deflection may be magnified by as much as the fifth power as reflected in the new flow rate.

As seen in FIG. 6, the left side structure 100a includes a transition zone 125 between the lower portion 104c of the side wall 104a and the lower wall 125a of the trunnion. In accordance with this invention, the side wall is reasonably uniform in cross sectional thickness except for the transition zone 125. As shown, the transition zone 125 has a width, as measured from any point on the inside surface 128 to the nearest point on the outside surface 129 which is not greater than substantially 150% of cross section of the side wall other than in the transition zone.

It is to be noted that the corner 130 formed on the inside surface between the inner face of the lower side wall 104c and the lower wall 125a represents a stress concentration point. While such a stress concentration point may be tolerated if the transition zone is dimensioned as discussed, the stress concentration point may be eliminated as shown in the left side wall 100*b* in which the transition zone 130 is of essentially the same cross sectional thickness as the adjacent sections of the side wall, i.e., the cross section of the transition zone, measured as described is less than 150% of the cross section of the adjacent side wall and is preferably of the same dimension as the side wall.

Another cost comparison would be the production cost of the newly modified part when compared to the cost of the original part. A weight savings of 30 percent, for example, will typically translate into an overall production cost savings in the range of 20 percent. The reason is that the cost of raw material is a large fraction of the total production cost. A significant additional saving in production cost will also be realized because the new design should run at a faster production cycle. This is because the part, due to certain wall portions which are generally thinner, and also because the thickened part is subjected to two dimensional cooling and not one dimensional cooling, will require less cooling time.

The following data represent a comparison of the clamp of this invention to the commercially available clamps, identified by source.

| Company | Length Cm | Weight gm | Wt/Length gm/cm |
|---|---|---|---|
| Baxter | 5.6 | 4.25 | 0.759 |
| Abbott | 5.6 | 4.00 | 0.714 |
| IVAC | 5.6 | 4.00 | 0.714 |
| McGaw | 5.6 | 4.00 | 0.714 |
| Imed | 5.6 | 4.00 | 0.714 |
| This Invention | 5.6 | 2.20 | 0.393 |

These data demonstrate the marked difference in weight to length ratio of the several clamps and the fact that the clamp having the lowest weight to length ratio, other than the clamp of this invention, has almost twice the weight to length ratio of the clamp of this invention. The clamp of this invention also has a length to weight ratio markedly less than that of the Clinico clamp (0.594 grams per centimeter, and apparently made of a less dense material.

All of the advantages of the new design will be retained provided the gate(s) is/are properly located. One logical location would be for the plastic to be symmetrically injected into the cavity at one end of the wheel axle guide surface of the housing (edge gate). For this location, the injected plastic flow passage has a shape close to ideal, that of an approximately circular cross-section and not too small. This flow tunnel can then "feed" the thinner side walls and the remaining portions of the housing cavity as may be required. An alternate location for the gate(s) would have the plastic enter at one end of the bottom clamping surface of the housing (also edge gating may be considered). Here too, the flow cross-section is generous and has excellent access to the thin side walls. To assure a part with symmetrical properties, usually two gates are used on opposite sides of the cavity or one larger gate centrally located. such central location usually being at the center of the bottom clamping surface.

In essence, the low cost improvement requires a relatively modest change in the cavity involving shaving the contact surface of the two halves and slightly enlarging the wheel axle surface. In addition, a slight shift of the core with respect to the cavity in the range of 20 percent to 70 percent of the original top wall thickness in a direction so as to thicken the top wall and thin the bottom wall. The potential economic benefits derived from a mold change approach, as contrasted to constructing new molds to reflect the improved design, are relatively large. This is because those firms who may derive immediate benefits already have large production molds and have substantial market shares. Modification of their molds can be done at a very modest cost and with very modest down time required for conversion.

It should be understood that this invention is not limited to the detailed descriptions set forth herein which describe in detail preferred forms of the present invention. Modifications thereof will be apparent to those skilled in the art, based on the above detailed disclosure, but such modifications based on this disclosure may not be deemed to depart from the spirit and scope of the present invention as set forth in the appended claims.

What is claimed is:

1. A roller pinch claw assembly for use in an I.V. set comprising:

a plastic injection molded housing including upper and lower left side walls, upper and lower right side walls, a top wall, a bottom wall between said left and right lower side walls, and left and right wheel guides, said housing dining a longitudinal axis, said top wall defining a central opening that extends along a portion of said housing, said left and right upper wheel guides each including a top wheel guide surface and a lower wheel guide surface, said left and right upper side walls defining said respective left and right wheel guides and extending below said top wall towards said respective left and right lower side walls, said bottom wall defining a pinching surface and a longitudinally extending relief groove, a roller wheel mounted for movement generally along the longitudinal axis of said housing, said roller wheel having a wheel axle that is received in said left and right wheel guides, said roller wheel having a dimension such as to leave a tube-clamping space between the bottom wall and the opposite facing section of said roller wheel, a portion of said roller wheel extending upward Through the central opening defined in the top wall, and said left and right wheel guides, said central opening defined in tie top wall, and said relief groove defined in said bottom wall, together, defining a flow control region extending longitudinally along the clamp assembly, a deformable plastic tube received in said housing and including a portion located in the tube-clamping space, said tube having a wall tat defines a lumen, at least a portion of said bottom wall having a cross-sectional thickness that is greater than the maximum cross-sectional thicknesses of said left and right lower side walls, along the length of said flow control region, said top wall having a cross-sectional thickness that is greater than that of the portion of said bottom wall defining the pinching surface, along the length of said flow control region, each of said left and right upper and lower side walls having a maximum thickness between 0.8 and 2.5 times the thickness of the wall of said tube, in the tube's uncompressed condition, along the length of said flow control region.

2. A roller pinch clamp assembly as set forth in claim 1 wherein each of said left and right upper side walls has a maximum cross-sectional thickness less than that of the top wall, along the length of said flow control region.

3. A roller pinch clamp assembly as set forth in claim 1 wherein:
   the ratio of the maximum cross-sectional thickness of said top wall to the uncompressed wall thickness of said tube is in the range of 2.5 to 4.5, along the length of said flow control region,
   the ratio of the maximum cross-sectional thickness of side walls to the uncompressed wall thickness of said tube is in the range of 1.1 to 2.3, along the length of said flow control region, and
   the ratio of the maximum cross-sectional thickness of the portion of the bottom wall defining the pinch surface to the uncompressed wall thickness of said tube is in the range of 1.2 to 2.5, along the length of said flow control region.

4. A roller pinch clamp assembly as set forth in claim 1 wherein each of said left and right lower side walls has a uniform cross-sectional thickness, along the length of said flow control region.

5. A roller pinch clamp assembly as set forth in claim 1 wherein:
   said left and right upper side walls are joined to said respective left and right lower side walls,
   said left and right upper side walls each have a cross-sectional thickness which is less than the cross-sectional thickness of said top wall, along the length of said flow control region,
   left and right transition zones are defined on the outside portion of said housing, at the intersection between said left lower and upper side walls, and at the intersection between said right lower and upper side walls, said left and right transition zones extending along the length of said left and right wheel guides,
   said left and right transition zones each include an inside surface and an outside surface, and
   said left and right transition zones each include a curved surface whose cross-sectional thickness, as measured from the inside surface to the nearest point on the outside surface, is not greater tin 150% of the thickness of the corresponding lower side wall, along the length of said flow control region.

6. A roller pinch clamp assembly as set forth in claim 1, wherein the top wall has a cross-section whose width to height ratio is less than 2.0, along the length of said flow control region.

7. A roller pinch clamp assembly as set forth in claim 1, wherein
   said clamp assembly has a region of no flow control between an entrance section of the housing and a shutoff position, and
   the top, side and bottom walls all have reduced thickness in the region of no flow control, as compared to the thicknesses of said walls in regions where the tube is pinched to achieve flow control or shut off.

8. A roller pinch clamp assembly as set forth in claim 1 wherein:
   said left and right upper side walls are joined to said respective left and right lower side walls,
   left and right transition zones are defined on the outside portion of said housing, at the intersection between said left lower and upper side walls, and at the intersection between said right lower and upper side walls,
   said left and right transition zones each include a curved surface whose cross-sectional thickness progressively increases from the corresponding left or right upper side wall to a maximum and progressively decreases from said maximum to the corresponding left or right lower side,
   the portion of said bottom wall defining the pinching surface has a maximum cross-sectional thickness that is greater than the maximum cross-sectional thickness of said upper side wall along the length of said flow control region, and
   said top wall cross-sectional thickness exceeds the maximum cross sectional thicknesses of said left and right upper and lower side walls by a ratio of 1.3 to 4.0, along the length of said flow control region.

9. A roller pinch clamp assembly as set forth in claim 1 wherein said clamp assembly is a parallel-acting clamp, and said bottom wall and said roller wheel cooperate to act upon said deformable tube and thereby vary the size of the lumen of said tube.

10. A roller pinch clamp assembly as set forth in claim 1 wherein:
    said pinch clamp assembly includes a flow control region, and
    the cross-sectional thickness of the left and right upper and lower side walls in said flow control region is less than two thirds the cross-sectional thickness of the top wall, along the length of said flow control region.

11. A roller pinch clamp assembly as set forth in claim 1 wherein said left and right upper side walls each have a cross-sectional thickness between 1.1 and 2.3 times the thickness of the wall of said plastic tube, along the length of said flow control region.

12. A roller pinch clamp assembly as set forth in claim 1 wherein said left and right lower side wails each have a cross-sectional thickness between 1.1 and 2.3 times the thickness of the wall of said plastic tube, along the length of said flow control region.

13. A roller pinch clamp assembly as set forth in claim 1 wherein:
    said left and right upper side walls are joined to said respective left and right lower side walls,
    left and right transition zones are defined on the outside portion of said housing at the intersection between said left lower and upper side walls, and at the intersection between said right lower and upper side walls,
    said left and right transition zones each include a curved surface whose cross-sectional thickness progressively increases from the corresponding left or right upper side wall to a maximum and progressively decreases from said maximum to the corresponding left or right lower side wall, and
    the cross-sectional thickness of said top wall is between 1.3 and 4.0 times fie cross-sectional thickness of the left and right lower side walls, along the length of said flow control region.

14. A roller pinch clamp assembly as set forth in claim 13 wherein said bottom wall and said roller wheel cooperate to act upon said deformable tube and thereby vary the size of the lumen of said tube.

15. A roller pinch clamp assembly as set forth in claim 13 wherein said clamp assembly is a parallel-acting clamp, and said bottom wall and said roller wheel cooperate to act upon said deformable tube and thereby vary the size of the lumen of said tube.

16. A roller pinch clamp assembly as set forth in claim 1 wherein the maximum cross-sectional thicknesses of each of said left and right upper and lower side walls is less than the maximum cross-sectional thickness of the portion of said bottom wall defining the pinching surface, along the length of said flow control region.

17. A roller pinch clamp assembly as set forth in claim 16 wherein the maximum cross-sectional thicknesses of said left upper and lower side walls and said right upper and lower side walls all are less than two thirds the maximum cross-sectional thicknesses of said top wall and the portion of said bottom wall defining the pinching surface, along the length of said flow control region.

18. A roller pinch clamp assembly as set forth in claim 1 wherein:
   said housing has a volume to length ratio of between 0.17 and 0.39 cubic centimeters per centimeter, and
   said housing has a strength capable of filly pinching shut a polyvinyl chloride tubing having an I.D. of between 2.18 mm and 3.18 mm and an O.D. of between 3.0 mm and 6.0 mm, and having a Shore D hardness in the range of 65 to 90.

19. A roller pinch clamp assembly as set forth in claim 12 wherein said bottom wall and said roller wheel cooperate to act upon said deformable tube and thereby vary the size of the lumen of said tube.

20. A roller pinch clamp assembly as set forth in claim 1 wherein each of said left and right upper side walls has a cross-sectional thickness less than the maximum cross-sectional thickness of the portion of said bottom wall defining the pinching surface, along the length of said flow control region.

21. A roller pinch clamp assembly as set forth in claim 20 wherein said bottom wall and said roller wheel cooperate to act upon said deformable tube and thereby vary the size of the lumen of said tube.

22. A roller pinch clamp assembly as set forth in claim 1 wherein:
   said clamp assembly has a range of wheel travel over which flow through said tube may be adjusted,
   said roller wheel travels in a parallel relationship relative to said bottom wall over the range of wheel travel in which flow through said tube may be adjusted, and
   said pinch clamp assembly is configured to vary the size of the lumen formed in use.

23. A roller pinch clamp assembly as set forth m claim 22 wherein:
   a clearance is defined between said roller wheel and said bottom wall and
   said clearance is of a dimension less than twice the undeformed wall thickness of said tube, along the length of said flow control region.

24. A roller pinch clamp assembly for use in an I.V. set comprising:
   a housing having a bottom wall, left and right spaced-apart side walls extending upwards from said bottom wall to form a generally U-shaped cross section, each of said left and right side walls including an upper side wall portion and a lower side wall portion, said left and right lower side wall portions defining an inner cavity to receive a hollow tube therein, said left and right upper side wall portions being generally parallel to and spaced laterally outward relative to said left and right lower side wall portions, to partially define an elongated groove extending along the length of said upper side wall portions, left and right upper rails extending inwardly from said respective left and right upper side wall portions, to form a top wall, said rails forming the upper surface of said grooves, said housing defining a longitudinal axis, and a central opening being defined in the top wall, extending along a portion of the length of said housing, and a roller opposite said bottom wall, said roller having an outwardly extending axle which is received in said grooves to direct travel of said roller along the longitudinal axis of said housing, in a housing flow control region, to control flow of fluid through said tube, said axle bearing against said side rails when compressing said tube, a portion of said roller extending upwardly through the central opening defined in the top wall, said upper rails having a predetermined thickness sufficient to resist significant deflection of said rails away from said bottom wall when said roller compresses said tube, said side wall portions having a narrowed thickness such that the thickness of each upper rail is about 1.3 to 4.0 times larger than the maximum thickness of each side wall potion, along the length of said flow control region, and such that the thickness of at least a portion of the bottom wall is larger than the maximum thickness of each side wall portion, along the length of said flow control region, between the left and right lower side wall portions, whereby said housing is farmed to minimize the amount of plastic material in the housing while maintaining the effectiveness of the clamp to properly resist the applied forces and provide suitable control of the flow of fluid through said tube, said bottom wall and said top wall being of substantially uniform cross-section along their length, and each of said left and right upper and lower side walls having a maximum thickness between 0.8 and 2.5 times the thickness of the wall of said tube, in its uncompressed condition, along the length of said flow control region.

25. A roller pinch clamp assembly for use in an I.V. set comprising:
   a plastic injection molded housing including spaced-apart left and right side walls, a top wall, a bottom wall, and spaced trunnions above said bottom wall, said housing defining a longitudinal axis, said top wall defining a central opening mat extends along a portion of the length of said housing,
   said bottom wall defining a pinching surface and a longitudinally extending relief groove,
   a roller wheel mounted for movement generally along the longitudinal axis of said housing, said roller wheel having a wheel axle that is received in and travels in said trunnions, a portion of said roller wheel extending upwardly through the central opening defined in the top wall,
   said wheel having a dimension such as to leave a tube clamping space between the bottom wall and the opposite facing section of said wheel,
   said trunnions, said central opening defined in the top wall and said relief groove defined in said bottom wall, together, defining a flow control region extending longitudinally along the clamp assembly,
   a deformable plastic tube received in said housing and including a portion located in the tube clamping space between said bottom wall and said wheel, said tube having a wall that defines a lumen,
   said left and right side walls each including a lower side wall and an upper side wall, the upper side wall defining one of the trunnions,
   left and right transition zones being defined between said respective left and right upper and lower side walls, the ratio of the cross-sectional thickness of the top wall to the maximum cross-sectional thickness of said left and right upper and lower side walls being in the range of 1.3 to 4.0, along the length of said flow control region, and each of said left and right upper and lower side walls having a maxim thickness between 0.8 and 2.5 times the thickness of the wall of said tube, in the wall's uncompressed condition, along the length of said flow control region.

26. A roller pinch clamp assembly as set forth in claim 25 wherein said clamp assembly is a parallel-acting clamp, and said bottom wall and said roller wheel cooperate to act upon said deformable tube and thereby vary the size of the lumen of said tube.

27. A roller pinch clamp assembly for use in an I.V. set comprising:

a plastic injection molded housing including spaced-apart left and right side walls, a top wall, a bottom wall, and left and right upper wheel guides, said housing defining a longitudinal axis, said top wall defining a central open that extends along a portion of the length of said housing, said bottom wall defining a pinching surface and a longitudinal extending relief groove, a roller wheel mounted for movement generally along the longitudinal axis of said housing, said roller wheel having a wheel axle that is received in said wheel guides, a portion of said roller wheel extending upwardly through the central opening defined in the top wall, said wheel having a dimension such as to leave a tube clamping space between the bottom wall and the opposite facing section of said wheel, said left and right upper wheel guides, said central opening defined in the top wall, and said relief groove defined in said bottom wall, together, defining a flow control region extending longitudinal along the clamp assembly, a definable plastic tube received in said housing and including a portion located in the tube clamping space between said bottom wall and said wheel, said tube having a wall that defines a lumen, said left and right side walls each including an upper side wall and a lower side wall, and a transition zone therebetween, the ratio of the cross-sectional thickness of the top wall to the maximum cross-sectional thickness of the left and right lower side walls being in the range of 1.3 to 4.0, along the length of said flow control region, each of said left and right lower side walls being of the same cross-sectional thickness, along the length of said flow control region, and each of said left and right lower side walls having a cross-sectional thickness less than the maximum cross-sectional thickness of the portion of said bottom wall defining the pinch surface, along the length of said flow control region, each of said left and right upper and lower side walls having a maximum thickness between 0.8 and 2.5 times the thickness of the wall of said tube, in the tube's uncompressed condition, along the length of said flow control region.

28. A roller pinch clamp assembly as set forth in claim 27 wherein said clamp assembly is a parallel-acting claim, and said bottom wall and said roller wheel cooperate to act upon said deformable tube and thereby vary the size of the lumen of said tube.

29. A roller pinch clamp assembly for use in an I.V. set comprising:

a plastic injection molded housing including spaced-apart left and right side walls, a top wall, a bottom wall, and left and right upper wheel guides, said housing defining a longitudinal axis, said top wall defining a central opening that extends along a portion of the length, of said housing, said bottom wall defining a pinching surface and a longitudinally extending relief groove, a roller wheel mounted for movement generally along the longitudinal axis of said housing, said roller wheel having a wheel axle that is received in said left and right wheel guides, a portion of said roller wheel extending upwardly through the central opening defined in tie top wall, said wheel having a dimension such as to leave a tube clamping space between the bottom wall and the opposite facing section of said wheel, said left and right upper wheel guides, said central opening defined in the top wall, and said relief groove defined in said bottom wall, together, defining a flow control region extending longitudinally along the clamp assembly, a deformable plastic tube received in said housing and including a portion located in the tube clamping space between said bottom wall and said wheel, said tube having a wall that defines a lumen, said left and right side walls each including an upper side wall and a lower side wall and a transition zone therebetween, the ratio of the cross-sectional thickness of the top wall to the maximum cross-sectional thickness of the left and right upper and lower side walls being in the range of 1.3 to 4.0, along the length of said flow control region, said top wall having a maximum cross-section thickness greater than than maximum cross-sectional thickness of the portion of said bottom wall defining the pinching surface, along the length of said flow control region, and said housing having a volume to length ratio in the range of 0.17 to 0.39 cubic centimeters per centimeter.

30. A roller pinch clamp assembly as set forth in claim 29 wherein said clamp assembly is a parallel-acting clamp, and said bottom wall and said roller wheel cooperate to act upon said deformable tube and thereby vary the size of the lumen of said tube.

31. A roller pinch clamp assembly as set forth in claim 29 wherein said housing volume to length ratio is 0.25 to 0.33 cubic centimeters per centimeter.

32. A roller pinch clamp assembly for use in an I.V. set comprising:

a plastic injection molded housing including spaced-apart left and right side walls, a top wall, and a bottom wall, said housing defining a longitudinal axis, said top wall defining a central opening that extends along a portion of the length of said housing, trunnions in each of said left and right side walls, below said top wall said bottom wall defining a pinching surface and a longitudinally extending relief groove, a roller wheel mounted for movement generally along the longitudinal axis of said housing, said roller wheel having a substantially cylindrical wheel axle that is received in said trunnions, a portion of said roller wheel extending upwardly through the central opening defined in the top wall, said wheel having a dimension such as to leave a tube clamping space between the bottom wall and tie opposite facing section of said wheel, said trunnions, said central opening defied in the top wall, and said relief groove defined in said bottom wall together, defining a flow control region extending longitudinally along the clamp assembly, a deformable plastic tube received in said housing and including a portion located in the tube clamping space between said bottom wall and said wheel, said tube having a wall that defines a lumen, said left and right side walls each including an upper side wall and a lower side wall, with a transition zone therebetween, the maximum cross-sectional thickness of said left and right upper and lower side walls being less than the maximum cross-sectional thickness of said top wall and the maximum cross-sectional thickness of the portion of said bottom wall defining the pinching surface, along the length of said flow control region, the maximum cross-sectional thickness of said top wall being greater than the maximum cross-sectional thickness of the portion of said bottom wall defining the pinching surface, along the length of said flow control region, and said housing having a volume to length ratio of between 0.17 and 0.39 cubic centimeters per centimeter.

33. A roller pinch clamp assembly as set forth in claim 32 wherein said clamp assembly is a parallel-acting clamp, and said bottom wall and said roller wheel cooperate to act upon said deformable tube and thereby vary the size of the lumen of said tube.

34. A roller pinch clamp assembly as set for in claim 32 wherein said housing has a volume to length ratio in the range of 0.25 to 0.33 cubic centimeters per centimeter.

35. A roller pinch clamp assembly for use in an I.V. set comprising:

a plastic injection molded housing including spaced-apart left and right side walls, a top wall, a bottom wall, and left and right wheel guides, said housing defining a longitudinal axis, said top wall defining a central opening that extends along a portion of the length of said housing, each of said side walls including an upper side wall that defines the wheel guide and a lower side wall extending from said bottom wall towards said upper wall, said bottom wall defining a pinching surface and a longitudinally extending relief groove, a roller wheel mounted for movement generally along the longitudinal axis of said housing, said roller wheel having a wheel axle that is received in said left and right wheel guides, a portion of said roller wheel extending upwardly through the central opening defined in the top wall, said wheel having a dimension such as to leave a tube clamping space between the bottom wall and the opposite facing section of said wheel, said left and right wheel guides, said central opening defined in the top wall and said relief groove defined in said bottom wall, together, defining a flow control region extending longitudinally along the clamp assembly, a deformable plastic tube received in said housing and including a portion located in the tube clamping space and between said bottom wall and said wheel, said tube having a wall that defines a lumen, the ratio of the cross-sectional thickness of the top wall to the maximum cross-sectional thickness of the left and right upper and lower side walls each being in the range of 1.3 to 4.0, along the length of said flow control region, said left and right upper and lower side walls each having a maximum thickness that is between 0.8 and 2.5 times the thickness of the wall of said tube when in the uncompressed condition, along the length of said flow control region, the maximum cross-sectional thickness of the left and right upper and lower side walls being less than the maximum cross-sectional thickness of the portion of said bottom wall defining the pinching surface, along the length of said flow control region, the maximum cross-sectional thickness of said top wall being greater than the maximum cross-sectional thickness of the portion of said bottom wall defining the pinching surface, along the length of said flow control region, and said housing having a volume to length ratio between 0.17 and 0.39 cubic centimeters per centimeter.

36. A roller pinch clamp assembly as set forth in claim 35 wherein said housing volume to length ratio is 0.25 to 0.33 cubic centimeters per centimeter.

37. A roller pinch clamp assembly as set forth in chum 35 wherein:

said housing includes a small end and a larger open end with a center portion therebetween, and said top wall has a cross-sectional thickness in at least one of said small end and said open end which is less than the cross-sectional thickness of the top wall in said center portion of said housing.

38. A roller pinch clamp assembly as set forth in claim 35 wherein said clamp assembly is a parallel-acting clamp, and said bottom wall and said roller wheel cooperate to act upon said deformable tube and thereby vary the size of the lumen of said tube.

* * * * *

UNITED STATES PATENT AND TRADEMARK OFFICE
CERTIFICATE OF CORRECTION

PATENT NO. : 6,422,529 B1
DATED : July 23, 2002
INVENTOR(S) : Kenneth N. Adelberg It is certified that error appears in the above-identified patent and that said Letters Patent is hereby corrected as shown below:

Column 3,
Line 16, "pinch, The" should be -- pinch. The --.

Column 5,
Line 63, "priority to the" should be -- priority to, the --.

Column 7,
Line 28, "modes)" should be -- modes --.

Column 8,
Line 16, "than of" should be -- than that of --.

Column 9,
Line 39, "which when" should be -- which, when --.
Line 48, "An:exist" should be -- exist, --.
Line 50, "the load and" should be -- the load, and --.

Column 14,
Line 12, "3l" should be -- 31 --.

Column 15,
Line 8, "zone which includes" should be -- zone includes --.
Line 30, "of, or, ideally," should be -- of, or ideally --.

Column 16,
Line 50, ", however," should be -- ; however, --.
Line 52, ", in turn presses" should be -- , in turn, presses --.

Column 21,
Line 2, "cross sectional" should be -- cross-sectional --.
Line 16, "thinner, and" should be -- thinner and --.
Line 56, "located. such" should be -- located, such --.

UNITED STATES PATENT AND TRADEMARK OFFICE
CERTIFICATE OF CORRECTION

PATENT NO. : 6,422,529 B1
DATED : July 23, 2002
INVENTOR(S) : Kenneth N. Adelberg It is certified that error appears in the above-identified patent and that said Letters Patent is hereby corrected as shown below:

Column 22,
Line 15, "claw" should be -- clamp --.
Line 21, "dining" should be -- defining --.
Line 40, "Through" should be -- through --.
Line 43, "tie" should be -- the --.
Line 49, "tat" should be -- that --.

Column 23,
Line 40, "tin" should be -- than --.
Line 51, "shutoff" should be -- shut-off --.
Line 52, "thickness" should be -- thicknesses --.

Column 24,
Line 10, "cross sectional" should be -- cross-sectional --.
Line 24, "two thirds" should be -- two-thirds --.
Line 33, "wails" should be -- walls --.
Line 52, "fie" should be -- the --.

Signed and Sealed this

Eleventh Day of February, 2003

JAMES E. ROGAN
*Director of the United States Patent and Trademark Office*

UNITED STATES PATENT AND TRADEMARK OFFICE
CERTIFICATE OF CORRECTION

PATENT NO.      : 6,422,529 B1
DATED           : July 23, 2002
INVENTOR(S)     : Kenneth N. Adelberg It is certified that error appears in the above-identified patent and that said Letters Patent is hereby corrected as shown below:

<u>Column 25,</u>
Line 6, "two thirds" should be -- two-thirds --.
Line 14, "filly" should be -- fully --.
Line 43, "m" should be -- in --.

<u>Column 26,</u>
Line 17, "potion" should be -- portion --.
Line 23, "farmed" should be -- formed --.
Line 41, "mat" should be -- that --.

<u>Column 27,</u>
Line 7, "maxim" should be -- maximum --.
Line 22, "open" should be -- opening --.
Lines 25 and 39, "longitudinal" should be -- longitudinally --.
Line 41, "definable" should be -- deformable --.
Line 67, "claim" should be -- clamp --.

<u>Column 28,</u>
Line 19, "tie" should be -- the --.
Line 41, "than" should be -- the --.

<u>Column 29,</u>
Line 6, "tie" should be -- the --.
Line 8, "defied" should be -- defined --.
Line 38, "for" should be -- forth --.

<u>Column 30,</u>
Line 43, "chum" should be -- claim --.

Signed and Sealed this

Twenty-second Day of April, 2003

JAMES E. ROGAN
*Director of the United States Patent and Trademark Office*